United States Patent

Castro et al.

[11] 4,185,096
[45] Jan. 22, 1980

[54] NOVEL DERIVATIVES OF PEPSTATIN, THEIR PREPARATION AND COMPOSITIONS CONTAINING THEM

[75] Inventors: Bertrand Castro, Messein; Jöel Menard, Paris; Geneviéve Evin, Nancy; Pierre Corvol, Paris, all of France

[73] Assignee: Agence Nationale de Valorisation de la Recherche (ANVAR), Neuilly Sur Seine, France

[21] Appl. No.: 929,562

[22] Filed: Jul. 31, 1978

[30] Foreign Application Priority Data

Aug. 4, 1977 [FR] France .............................. 77 24093

[51] Int. Cl.² ...................... A61K 37/00; C07C 103/52
[52] U.S. Cl. ............................... 424/177; 260/112.5 R
[58] Field of Search .................. 260/112.5 R; 424/177

[56] References Cited

U.S. PATENT DOCUMENTS

| 3,840,516 | 10/1974 | Umezawa et al. | 260/112.5 R |
|---|---|---|---|
| 3,867,364 | 2/1975 | Umezawa et al. | 260/112.5 R |
| 3,869,347 | 3/1975 | Umezawa et al. | 260/112.5 R |
| 3,878,185 | 4/1975 | Murao et al. | 260/112.5 R |

*Primary Examiner*—Delbert R. Phillips
*Attorney, Agent, or Firm*—Oblon, Fisher, Spivak, McClelland & Maier

[57] ABSTRACT

The novel derivatives of pepstatin have the general formula (I) below in which X, Y and Z, are identical or different, and each represent an amino-acid selected from arginine, glutamic acid, aspartic acid, lysine, histidine and valine, the carboxyl function of the terminal amino-acid being esterifiable. The indices a, b and c are each equal to zero or 1, the sum a+b+c being equal to 1, 2 or 3. The invention also includes the water soluble salts and their preparation, and the compositions containing them.

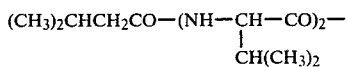

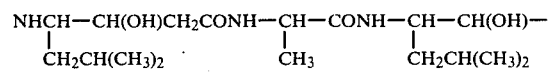

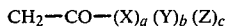

These novel products are particularly useful in the diagnosis and treatment of arterial hypertension due to the action of renine.

10 Claims, No Drawings

NOVEL DERIVATIVES OF PEPSTATIN, THEIR PREPARATION AND COMPOSITIONS CONTAINING THEM

The present invention relates to novel derivatives of pepstatin of the general formula:

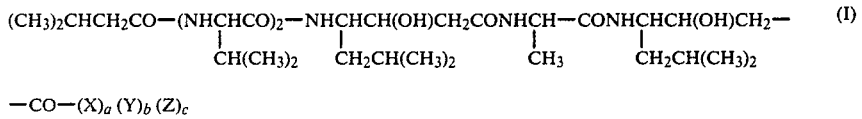

$$-CO-(X)_a(Y)_b(Z)_c$$

their salts, their preparation and compositions containing them.

In the general formula (I) each of the symbols X, Y and Z which are identical or different, represent an amino-acid residue selected from arginine, glutamic acid, aspartic acid, lysine, histidine or valine, forming with the free carboxyl group of the pepstatin or of the adjacent amino-acid a peptide bond-CONH—; the carboxyl function of the terminal amino-acid may exist in free form or in the form of an ester of an aliphatic alcohol containing 1 to 4 carbon atoms, and the indices a, b and c are each equal to zero or 1, the sum a+b+c being equal to 1, 2 or 3.

In the foregoing, the amino-acids defined by X, Y and Z are preferably present in their natural form, that is to say in the L form.

When the terminal carboxyl function is free, the present invention relates also to the salts of the compounds of general formula (I) with solubilizing bases so that the solubility in water of the salts obtained is higher than or equal to about 0.4% weight by volume. As the solubilizing bases, preference is given to the use of amino-acids selected from arginine, lysine or α,γ-diaminobutyric acid.

The present invention also concerns the use as drugs, notably as inhibitors of the renin activity of the new pepstatin derivatives as hereinabove defined.

The invention also relates to pharmaceutical compositions containing, as active ingredient, a new pepstatin derivative of the invention.

The invention also relates to diagnosis and/or treatment of hypertensive attack due to an excessive secretion of renin.

The pepstatin, that is to say isovaleryl-L-valyl-L-valyl-4-amino-3-hydroxy-6-methyl-heptanoyl-L-alanyl-4-amino-3-hydroxy-6-methylheptanoic acid is a known product. Reference may be made to FR patent 70.21.557.

Certain pepstatin derivatives are already known, notably butyl-, propyl-, and acetyl-pepstatins which are mentioned in Chemical Abstracts no. 124.637 p. vol. 79 (1973).

According to the present invention, the novel derivatives of pepstatin of the general formula (I) may be obtained according to the usual methods used in peptide synthesis, that is to say by reacting pepstatin with a suitable amino-acid or a dipeptide or a tripeptide in the presence of a condensation agent, or again after having converted, by means of a suitable conventional reactant, such as isopropyl chloroformate, the carboxyl function of the pepstatin into a carbonic-carboxyl mixed anhydride. As condensation agent, there may be used more particularly dicyclohexylcarbodiimide, benzotriazolyloxy-tris-dimethylaminophosphonium hexafluorophosphate (B. Castro et al. Tetrahedron Letters 1219 (1975) or the Bates reagent (A. J. Bates et al. Helv. Chim. Acta, 58, 633 (1975). Generally, the reaction is carried out in an organic solvent, such as dimethylformamide or dimethylsulfoxide, at a temperature in the vicinity of 20° C. It is particularly advantageous to protect the functions which do not take part in the reaction by blocking groups, which are easily removable once the condensation reaction is terminated.

The salts of the product of general formula (I) may be obtained by shaking an aqueous suspension of a derivative of pepstatin of general formula (I) with the suitable solubilizing base in a stoichiometric amount at a temperature comprised between 20° and 40° C. until complete dissolution then by isolating the salt by any known separation method, and more particularly by liophilization.

The pepstatin used as a starting material is isovaleryl-L-valyl-L-valyl-4-amino-3-hydroxy-6-methyl-heptanoyl-L-alanyl-4-amino-3-hydroxy-6-methylheptanoic acid of the following formula:

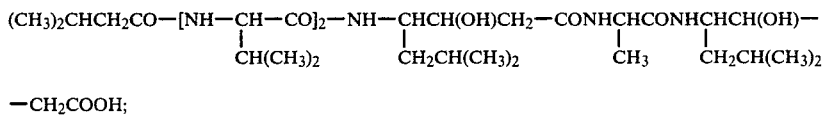

$$-CH_2COOH;$$

it may be prepared according to the process described in the French Patent Application 70.21.557.

This process for obtaining pepstatin consists in cultivating a strain of Streptomyces producing pepstatin, such as for example *Streptomyces testaceus, Streptomyces argenteolus* var. *toyokensis* et *Streptomyces caespitosus*, in a nutrient medium under aerobic conditions until a substantial inhibition activity of the pepsin is provided to said medium and in recovering said pepstatin from said medium.

The novel derivatives according to the present invention have a solubility in water which is distinctly higher than that of pepstatin. Although pepstatin is practically insoluble in water, the products of general formula (I) have generally a solubility higher than about 0.4%, that is to say at least 40 times greater than that of pepstatin.

As a matter of fact, it was noted that complete solubilization of pepstatin in water is obtained up to a concentration of 146 μm/l. On the contrary the solubility of methyl ester of pepstatin-arginine in water is 30 times higher whereas the one of the pepstatin-arginine is 50 times higher than the one of the pepstatin.

The novel derivatives according to the invention have the property of inhibiting the action of renin. Renin is a proteolytic enzyme produced and secreted by the kidney, which acts on the angiotensinogen of the plasma to provide an inactive decapeptide (angiotensin I), which, in its turn, is converted into an octapeptide (angiotensin II) which acts on the organism by causing an increase in blood pressure.

In vitro, the inhibition activity of the novel compounds according to the invention can be demonstrated by the action either on hog renin on a synthetic substrate constituted by a N-acetylated tetradecapeptide (Asp—Arg—Val—Tyr—Ile—His—Pro—Phe—His—Leu—Leu—Val—Tyr—Ser) by assaying the released tetrapeptide (Leu—Val—Tyr—Ser) by fluoroescamine fluorimetry, or on hog renin on a natural substrate constituted by rat angiotensinogen by the technic of J. Menard and K. J. Catt, Endocrinology, 90, 422 (1972).

In these two systems, the inhibition molar concentration of the compounds of the invention ($IC_{50}$) which reduces the activity of renin by 50% is generally comprised between $1.10^{-6}$ and $1.10^{-8}$.

In vivo, in the anaesthetized binephrectomized rat, into which 50 m GU/kg (50 milli Goldblatt units/kg) of purified hog renin is injected, the products according to the invention produce an inactivation of the plasma renin and a decrease of the blood pressure at doses comprised between 50 and 300 μg/kg by the intravenous route.

In addition, the novel products according to the invention have a low toxicity. In mice, the 50% lethal doses ($LD_{50}$) is generally higher than 800 mg/kg by the intraperitoneal route.

In the following, the compounds of the invention will be denoted by the name "pepstatin" followed by the name of the amino-acid, of the dipeptide or tripeptide to which the pepstatin is linked.

The following examples, given by way of non-limiting illustration, demonstrate how the invention can be practiced.

EXAMPLE 1

To 69 mg of pepstatin and 70 mg of the dihydrochloride of the methyl ester of arginine, are added 5 cm³ of dimethylformamide, 88 mg of benzotriazolyloxy-trisdimethylaminophosphonium hexafluorophosphate (called below BOP) and 50 mg of triethylamine are then added. The reaction mixture is stirred for 72 hours at a temperature close to 20° C. 15 cm³ of water and then 20 cm³ of a saturated aqueous solution of sodium chloride are then added. After cooling to a temperature in the vicinity of 0° C., the gelatinous precipitate is drained, washed ether and dried under reduced pressure (20 mm of mercury) at 20° C. The dry residue is dissolved in 50 cm³ of methanol. The solution is filtered and the filtrate is concentrated to dryness. In this way, 69 mg of the methyl ester of pepstatin-arginine are thus obtained, whose characteristics are as follows:
melting point ("Köfler" bank): 262°–263° C.
rotary power=$[\alpha]_D^{20}=-40.1°$ (c=0.18; methanol)
analysis (amino-acids) after hydrolysis with 6 N hydrochloric acid for 24 hours at 110° C.:
  arginine: 0.95
  alanine: 1
  valine: 2.10
infrared spectrum: characteristic "ester" band at 1740 cm$^{-1}$

EXAMPLE 2

In a mixture of 4 cm³ of dimethylformamide and 4 cm³ of dimethylsulfoxide, are added 100 mg of pepstatin and 100 mg of trifluoroacetate of benzyl ester of nitronine, 90 mg of BOP and 40 mg of triethylamine are then added. The reaction mixture is stirred for 6 days, 15 cm³ of water and then 20 cm³ of a saturated aqueous solution of ammonium sulfate are then added. After cooling to a temperature close to 0° C., the product is drained and then dissolved in a water hydrochloric acid- acetic acid mixture (19-1-80 by volume). The solution is subjected to hydrogenation at ordinary pressure in the presence of palladium on charcoal for 24 hours. The solution is filtered on "Celite". The filtrate is concentrated to dryness and the residue is taken up with 50 cm³ of isopropanol. After filtration of the insoluble residue, the filtrate is evaporated to dryness and the product obtained is dried. In this way, 60 mg of pepstatin-arginine are obtained of which the characteristics are as follows:
melting point (Köfler bank): above 250° C. (decomposition)
analysis (amino-acids) after hydrolysis by 6 N hydrochloric acid for 24 hours at 110° C.:
  alanine: 1
  valine: 1.96
  arginine: 1

EXAMPLE 3

Into 8 cm³ of a mixture of dimethylformamide and dimethylsulfoxide (3-1 by volume), 130 mg of pepstatin and 120 mg of the hydrochloride of tertiobutyl diester of glutamic acid are added. Then 180 mg of BOP and 45 mg of triethylamine are added. After 72 hours of stirring, 15 cm³ of distilled water are added. The precipitate is drained and washed with 15 cm³ of ethyl ether. The product is redissolved in 30 cm³ of methanol. The insoluble residue is separated by filtration and the filtrate is evaporated. Then 10 cm³ of a mixture of methylene chloride-trifluoroacetic acid (1:1 by volume) are added, then it is allowed to stand for 30 minutes at a temperature close to 20° C. The mixture is concentrated almost to dryness. Ether is then added. The precipitate formed is separated by filtration and then washed with ether. After drying, 130 mg of pepstatin-glutamic acid are obtained whose characteristics are as follows:
melting point (Köfler bank): 230° C.,
rotary power: $[\alpha]_D^{20}=79.0°$ (c=0.55; methanol)
analysis (amino-acids) after hydrolysis with 6 N hydrochloric acid for 24 hours at 110° C.:
  alanine: 1
  valine: 1.97
  glutamic acid: 0.99.

EXAMPLE 4

Operating as in Example 3, but starting with 137 g of pepstatin, 98 mg of hydrochloride of tertiobutyl diester of aspartic acid, 177 mg of BOP and 68 mg of triethylamine in 8 cm³ of dimethylformamide, 109 mg of pepstatin-aspertic acid are obtained whose characteristics are as follows:
melting point ("Köfler" bank): 238°–240° C.
rotary power: $[\alpha]_D^{25}=-67.6°$ (c=0.51; methanol)
analysis (amino-acids) after hydrolysis with 6 N hydrochloric acid for 24 hours at 110° C.:
  aspartic acid: 0.92
  alanine: 1.12
  valine: 2

The present invention relates also to the pharmaceutical compositions which contain a derivative of pepstatin of the general formula (I) or one of its salts in association with one or several diluents or adjuvants which are compatible therewith and pharmaceutically acceptable. Preferably, the compositions according to the invention are administered by the parenteral route and more particularly by the intravenous route.

As compositions administerable by the parenteral route may more especially be used sterile solutions of the compounds of the general formula (I) in water or in a physiological isotonic solute. It is also possible to use solutions, suspensions or emulsions of the compounds of general formula (I) in suitable pharmaceutically acceptable solvents or vehicles. In this case, propyleneglycol, polyethylene glycol, vegetable oils (such as olive oil) or injectable organic esters (such as ethyl oleate), may be employed. It is possible to add to the composition wetting, emulsifying or dispersing agents. The sterilization can be done in various ways, for example by means of a bacteriological filter, by incorporating sterilizing agents with the composition or by irradiation. The compositions according to the invention can also be prepared in the form of sterile solid compositions which can be dissolved at the moment of use in sterile water or in any other injectable sterile medium.

The compositions according to the invention are particularly useful for evaluating the responsibility of the renin-angiotensin system in the pressure rise in hypertensive patients. The therapeutic treatment depends essentially on such analysis. A single dosage comprising between 1 and 30 mg/kg could be administered by the intravenous route. The inhibition of the plasma renin that results causes a drop in blood pressure if an excess of renin is the cause of the hypertension. On the basis of this data, a treatment blocking the renin-angiotensin system will be chosen. Novel compositions according to the invention are particularly useful in the urgent treatment of certain hypertensive subjects related to excessive secretion of renin. In acute treatment, the dosages are generally comprised between 1 and 30 mg/kg for an adult and may be administered in a single injection or by perfusion. The compositions according to the invention may also be utilized at lower dosages as a chronic treatment.

Generally, the physician will determine the treatment and the posology that he judges most suitable as a function of the degree of hypertension, the age, the weight and all factors appropriate to the patient to be treated.

The following example, given by way of non-limiting illustration, demonstrates a composition according to the invention.

EXAMPLE 500 mg of the compound according to Example 2 (pepstatin-arginine) are dissolved in 100 cm$^3$ of injectable solution. The solution is sterilized by filtration on a bacteriological filter and is aseptically divided into ampoules in the amount of 10 cm$^3$ per ampoule. The ampoules are sealed and they contain 50 mg of the active principle.

Results of pharmaceutical assays

A—Inhibition activity in vitro of methyl ester of pepstatin-arginine

1—On natural substrate 30 micro-Goldblatt units (30 μm GU) of purified hog renin [CORVOL et al. Cir. Res., 41, 616–622 (1977)] were incubated at pH 6.5 for 15 minutes, at 37° C. in the presence of an excess of rat renin substrate obtained from binephrectomized rats. Angiotensin I generated was measured by radioimmuno assay [MENARD and CATT Endocrinology, 90, 422–430 (1972)]

It was observed that in the above condition the methyl ester of pepstatin-arginine provides a 50% inhibition of renin activity at the concentration of about $10^{-7}$ mole/l.

The pepstatin also decreased in the same conditions the renin activity by 50% at the concentration of $10^{-7}$ mole/l.

2—On a synthetic substrate 10 milli-Goldblatt units of hog renin, from the same source as above, were incubated at pH 6 for one hour at 37° C. in the presence of a synthetic substrate constituted by a N-acetylated renin tetradecapeptide [GALEN et al. Biochem. Biophys. Acta, 523, 485–493 (1978)].

The tetrapeptide quantity produced per hour of incubation was measured by fluorimetry. Three different concentrations of N-acetylated tetradecapeptide were used, that is to say 2.3, 4.6 and 9.3 nmoles with increasing amounts of pepstatin or methyl ester of pepstatin-arginine (0.25, 0.50 and 0.75 $10^{-6}$ mole/l). The results were plotted according to the Dixon representation and it was so determinated that inhibition constant of methyl ester of pepstatin-arginine was $3.15 \times 10^{-7}$ mole/l whereas the one of the pepstatine was $10^{-7}$ mole/l.

B—Inhibition activity in vivo of methyl ester of pepstatin-arginine and of pepstatin-arginine The experimental model of renal hypertension developped in rats by ROJO-ORTEGA and GENEST [Can. J.Phys. Pharm. 46 883–885 (1968)] was used.

A complete ligature of the aorta between the renal arteries was performed in twenty male Sprague-Dawley rats, weighing 300 g. They were investigated between 5 and 10 days after surgery. The blood pressure was measured in the conscious unrestrained rats, through a carotid cannula inserted 24 hours before measurements were made.

The maximal decrease in blood pressure induced by an injection of "Saralasin" was compared [Sar 1, Ala-8 Angiotensin II] in the same animals, to the maximum fall in blood pressure induced by the soluble derivatives of pepstatin according to the invention.

Among 20 hypertensive rats (mean blood pressure: 157±4,37 mmHg), 13 rats had a blood pressure fall of 10 mmHg and more after the intravenous injection of Saralasin (140 nmoles). In these thirteen rats, the average blood pressure decrease was 44.5±8.5 mmHg. The intravenous injection of 350 nmoles of pepstatinyl-Arginine-O-Methyl Ester (2 rats), or the Arginine salt of Pepstatinyl (11 rats) decreased blood pressure by 48.3±8.2 mmHg. The maximal fall in blood pressure was obtained 5 minutes after Saralasin, and 6 minutes after soluble pepstatin. Blood pressure returned to the control level 10 minutes after the injection of both inhibitors.

Among 13 Saralasin-responders rats, one was resistant to pepstatin. Plasma renin concentration was very high in these 13 rats (501±125 pmoles of angiotensin I h$^{-1}$ ml$^{-1}$), by comparison with normotensive animals (5.8±1.8). Plasma renin concentration decreased to 289±74 pmoles of angiotensin I h$^{-1}$ ml$^{-1}$, 5 minutes after the intravenous injection of soluble pepstatin.

We claim:

1. A pepstatin derivative having the formula

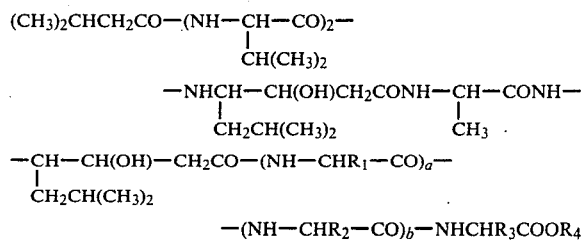

$$-CH-CH(OH)-CH_2CO-(NH-CHR_1-CO)_a-$$
$$\phantom{xxxx}|$$
$$\phantom{xx}CH_2CH(CH_3)_2$$

$$-(NH-CHR_2-CO)_b-NHCHR_3COOR_4$$

wherein $R_1$, $R_2$ and $R_3$ are each a side chain from an amino-acid selected from the group consisting of arginine, glutamic acid, aspartic acid, lysine, histidine and valine; $R_4$ is H or $C_1$-$C_4$ alkyl; and a and b are each zero or 1, the sum of a plus b being equal to 0, 1 or 2; and their salts with solubilizing bases.

2. The pepstatin derivative of claim 1, comprising the methyl ester of pepstatin-arginine whose characteristics are as follows:
melting point ("Köfler" bank)=262°-263° C.
rotatory power: $[\alpha]_D^{20}=40.1°$ (c=0.18; methanol)
analysis (amino-acids) after hydrolysis with 6 N hydrochloric acid for 24 hours at 110° C.:
arginine: 0.95
alanine: 1
valine: 2.10
infrared spectrum: characteristic "ester" band at 1740 cm$^{-1}$.

3. The pepstatin derivative of claim 1, comprising pepstatin-arginine whose characteristics are as follows:
melting point ("Kofler" bank) higher than 250° C. (decomposition)
analysis (amino-acids) after hydrolysis with 6 N hydrochloric acid for 24 hours at 110° C.:
alanine: 1
valine: 1.96
arginine: 1.

4. The pepstatin derivative of claim 1, comprising pepstatin-glutamic acid whose characteristics are as follows:
melting point ("Köfler" bank): 230° C.
rotatory power: $[\alpha]_D^{20}=-79.0°$ (c=0.55; methanol)
analysis (amino-acids) after hydrolysis with 6 N hydrochloric acid for 24 hours at 110° C.:
alanine: 1
valine: 1.97
glutamic acid: 0.99.

5. The pepstatin derivative of claim 1, comprising pepstatin-aspartic acid whose characteristics are as follows:
melting point ("Köfler" bank): 238°-240° C.
rotatory power: $[\alpha]_D^{25}=-67.6°$ (c=0.51 methanol)
analysis (amino-acids) after hydrolysis with 6 N hydrochloric acid for 24 hours at 110° C.:
aspartic acid: 0.92
alanine: 1.12
valine: 2.

6. An antihypertensive composition, comprising an amount effective to reduce hypertension of, a pepstatin derivative according to claim 1, in association with one or several compatible and pharmaceutically acceptable diluents or adjuvants.

7. A method of treatment of hypertension associated with an excessive secretion of renin, which comprises administering to a hypertensive patient the composition of claim 6.

8. The antihypertensive composition of claim 6, wherein said amount is from 1 to 30 mg/kg.

9. A method of diagnosing hypertension associated with an excessive secretion of renin, which comprises administering to a hypertensive patient a diagnostically effective amount of a pepstatin derivative according to claim 1, and observing the resultant change in blood pressure.

10. The pepstatin derivatives of claim 1, wherein said solubilizing bases are selected from the group consisting of arginine, lysine and α,γ-diamino butyric acid.